US012623026B2

(12) United States Patent
Marcoz

(10) Patent No.: US 12,623,026 B2
(45) Date of Patent: May 12, 2026

(54) INJECTION MONITORING MODULE

(71) Applicant: BIOCORP PRODUCTION S.A.S., Issoire (FR)

(72) Inventor: Alain Marcoz, Issoire (FR)

(*) Notice: Subject to any disclaimer, the term of this patent is extended or adjusted under 35 U.S.C. 154(b) by 626 days.

(21) Appl. No.: 18/002,778

(22) PCT Filed: Jun. 23, 2020

(86) PCT No.: PCT/IB2020/000580
§ 371 (c)(1),
(2) Date: Dec. 21, 2022

(87) PCT Pub. No.: WO2021/260404
PCT Pub. Date: Dec. 30, 2021

(65) Prior Publication Data
US 2023/0347066 A1    Nov. 2, 2023

(51) Int. Cl.
*A61M 5/315*    (2006.01)

(52) U.S. Cl.
CPC ...... *A61M 5/31553* (2013.01); *A61M 5/3158* (2013.01); *A61M 2205/3317* (2013.01)

(58) Field of Classification Search
CPC ........................ A61M 5/31553; A61M 5/3158
See application file for complete search history.

(56) References Cited

U.S. PATENT DOCUMENTS

2018/0154086 A1    6/2018    Toporek
2018/0200451 A1*   7/2018    Shekalim .............. G01F 11/029

FOREIGN PATENT DOCUMENTS

EP    2452712 A1    5/2012
EP    3103492 A1 * 12/2016    ........ A61M 5/31551
JP    2019526391 A    9/2019
WO    2014128156 A1    8/2014
WO    2017/013464 A1    1/2017
WO    2018013419 A1    1/2018
WO    2019/057911 A1    3/2019
WO    2019091890 A1    5/2019

OTHER PUBLICATIONS

ISR: European Patent Office; NL Nov. 25, 2020.

* cited by examiner

*Primary Examiner* — Dung T Ulsh
(74) *Attorney, Agent, or Firm* — Patshegen IP; Moshe Pinchas

(57)            ABSTRACT

An injection monitoring module for mounting onto the body of an injection pen system comprising a rotatable dose setting wheel, and an injection activator, and having a central longitudinal axis, the injection monitoring module comprising: a hollow main body comprising a central longitudinal bore; a magnetic field production means, located on the hollow main body, at the proximal extremity of the bore; an injection monitoring system comprising at least one magnetic sensor; an inner sleeve located within the bore, engaging with the outer surface of the dose wheel, and co-rotating therewith during dose setting, without axial translation; the inner sleeve being connected to the monitoring system to enable co-rotation of both the sleeve and monitoring system about the axis during dose setting, and translation of the monitoring system along the axis, without rotation, during injection of a drug from the pen.

22 Claims, 6 Drawing Sheets

9

56

13

11

1

14

7

4

3

2

5

INJECTION MONITORING MODULE

The present invention relates generally to monitoring systems for injectable drug delivery devices, and in particular to injection monitoring for injection pen systems.

Injection monitoring is a well known field associated with injectable drug delivery devices, especially with regard to infusion systems, for example. Over time, such monitoring systems have been transferred more recently to injection pen systems for delivery of a drug, enabling users of such pen injection systems, and health care professionals involved in the treatment and follow-up of such patients, to monitor more closely their own injection regimes, and in many cases, the doses actually administered, in an attempt to lead to better healthcare outcomes. These developments have been accompanied by the increased associated use of software and portable communications devices such as tablets or smartphones, which have been programmed to receive information from, and interact with, the monitoring systems in order to provide information to the user or healthcare professional on-the-fly, or at regular intervals via appropriate communications units included in the monitoring systems.

In regard to pen injection systems in particular, for example, one of the challenges has been to provide easy to use, reliable and fairly failsafe systems that can be adapted to the various different variants of such commercially available pen injection systems, of which there are many. Previous attempts at providing such monitoring systems have usually involved adapting the body of the pen injection system by including electronic components therein along with one or more sensors. One of the major disadvantages of such systems however, is that they tend to make the end product, once all of the electronic components have been integrated, into fairly bulky and unwieldy objects, and thus more difficult to use from a user perspective. Additionally, such modified systems tend to be very specific to a given brand or a manufacturer, and thus of little or no use with other manufacturers. Furthermore, in order to overcome the issues with bulkiness and unwieldiness of the modified pen injection systems, there has been a tendency to attempt to reduce the overall volume of the injection pen bodies as much of possible through miniaturisation of the complex electronic components, which in turn has brought about its own problems, in particular with regard to electromagnetic interference between the various components due to the close proximities of the circuits providing the required or desired integrated functionality. Moving the sensors in such monitoring systems further away from the source of electromagnetic interference only further complicates matters, potentially leading to erroneous readings, or requiring further systems to compensate for the physical separation of the sensors from the other electronic components, such as a micro-controller designed to control and command the various components and manage their interactions.

The injection pen systems in question are well known per se and are commonly equipped with a proximally located dose setting wheel and injection activator, the dose setting wheel being rotatable about a central longitudinal axis of the pen injection system. The wheel is rotated by the user to select the dose of drug to be administered. The pen is generally configured, either mechanically or electro-mechanically to effect an injection upon activation of an injection activator. Such injection activators are quite commonly a simple press or push-button, in mechanical or electrical contact with the dispensing mechanism located within the pen injection system, the pressing of which causes the injection mechanism to fire and inject the drug contained within the pen injection system. In some pen injector systems, the dose setting wheel is configured to rotate not only during dose setting, but also during injection. This is generally achieved through the inclusion of one or more metallic components, such as a helically wound drive spring located within a housing body of the injection pen system and physically coupled to the dose setting wheel. As such metallic elements are relatively large objects in comparison to the electronic component systems that are included in many pen injection systems today, these large metallic objects can further perturb signals that the sensors in such electronic component systems are designed to capture or pick up, rendering the systems potentially less accurate, and/or requiring that complex correction mechanisms be put in place to avoid calculation errors.

Some attempts at overcoming the difficulties of electronic component integration have already been described in the patent literature.

For example, published PCT patent application WO2014128156A1 relates to a sensor assembly having a first rotary sensor part with a plurality of individual electrically conducting sensor areas arranged in a pattern, a second rotary sensor part arranged rotationally relative to the first part, and comprising a plurality of contact structures adapted to be in contact with conducting sensor areas on the first sensor rotary part. The contact structures are configured to engage and connect different sensor areas as the first and second part of the rotary sensor rotate relative to each, the created connections being indicative of a rotational position between the first and second portions. One of the contact structures is an actuatable contact structure being axially moveable relative to the first portion and having a connected position in which the actuatable contact structure is in contact with a sensor area and a disconnected position in which the actuatable contact structure is not in contact with a sensor area. This system is housed within the pen injector body, at least partly within the volume inside the dose setting wheel. The system also comprises a visual display, such as an LCD display located on, or instead of, the injection activator button.

In comparison, published PCT application WO2018013419A1 relates to a dose detection system including a dosing component attached to an actuator and rotationally and axially moveable relative to a coupling component attached to a dose setting member, and comprising a module including an electronic sensor operative to detect a relative rotation of the coupling component and the dosing component to detect a dose delivered by the medication delivery device. The dose detection module is removably coupled to a proximal end of a pen injection system, and is intended to function as a means to detect the amount of medication dispensed by the pen injection system while attached thereto, store the detected dose in memory, and transmit a signal representative of the detected dose to a remote communication device. The system comprises a pair of rotatable and translatable cylinders that interact with each other via electrical contacts provided on the cylinder surfaces to denote various states or positions of the injection administration process including dose setting, the electrical contacts being connected to a collection of electronic components housed on a flexible printed circuit board, disposed in an accordion-style arrangement of superimposed folds within the removably couple body, and which is insulated between the overlapping layers of circuit board by an electrically non-conducting spacer layer to prevent potential electric, electronic and electromagnetic interference.

One immediate observation of the above-described configuration is that despite the use of a folded flexible printed circuit board to provide multiple surfaces on which to position the electronic components, their relative spatial density and positioning with regard to each other has necessitated that non-conducting spacers be provided between the layers of electronic componentry. The immediate consequence of this is an increased height in the module and a necessarily increased complexity of the clip-on dose detection module described therein.

Accordingly, one object of the present invention is to provide an injection monitoring module adapted and configured to be removably attached to a proximal extremity of an injection pen system for delivery of a drug, the injection pen system having a dose setting wheel that can be rotated about a central longitudinal axis of the pen injection system for setting a dose of drug to be injected, and fixed against rotation during injection, and wherein the injection monitoring module has a much simpler configuration, whilst at the same time obviating the need for complicated shielding or protecting solutions to counter any unwanted electrical, electronic, or electromagnetic effects caused by the relatively high density of the electronic components within the monitoring module.

Another object of the present invention is to provide an injection monitoring module as above, wherein said monitoring module is adapted and configured to determine an injection end point in a pen injection system in which the dose setting wheel does not rotate during injection. For the purposes of the present invention, the expression "injection end point" as used herein signifies not only the completion of an injection of a dose of injectable substance such as a drug, where a user injects a required dose of injectable substance in a single operation, but also includes any amount of drug actually ejected by the pen injection system, after selection, or dialling, of a dose via the dose setting wheel, when the injection monitoring module is mounted on the injection pen system. This means that if a user carries out a sequence of small repeat injection operations, for example, by repeated, successive activation of the injection activator, a corresponding end point for each injection step will be registered, and a corresponding amount of injectable substance calculated as having been injected or ejected from the pen injection system.

Yet another object of the invention is to provide an injection monitoring module as above, in which said module is adapted and configured to detect or calculate a dose or amount set by a user of injectable substance contained within the pen injection system, an injection beginning or start point and an injection end point in said pen injection system, and therefrom determine whether or not all of the dose or amount set by the user of the pen injection system has been ejected from said pen system.

These and other objects of the invention will become readily apparent from the complete reading of the current specification.

According to any of the above objects therefore, there is provided an injection monitoring module adapted and configured to be removably mounted to a proximal extremity of an injection pen system for delivery of a drug, the injection pen system having a pen body, a proximally located dose setting wheel connected to said body, and an injection activator, the dose setting wheel being rotatable about a central longitudinal axis of the pen injection system during dose setting and fixed against rotation during injection, wherein the injection monitoring module comprises:

a hollow main body adapted and configured to be coaxially mounted around the body of the pen injection system, the hollow main body comprising a central longitudinal bore having a proximal extremity and a distal extremity, and a central longitudinal axis;

a magnetic field production means, located on or within the hollow main body, at the proximal extremity of the central longitudinal bore;

an injection monitoring system comprising at least one or a plurality of magnetic sensors, the injection monitoring system being located at the proximal extremity of the bore of the hollow main body;

the hollow main body further comprising an inner sleeve located within the central longitudinal bore, and configured to frictionally engage with an outer surface of the dose setting wheel to co-rotate around the central longitudinal axis, without axial translation along said central longitudinal axis, with the dose setting wheel during dose setting; wherein the inner sleeve is connected to the injection monitoring system; and the connection between the inner sleeve and the injection monitoring system is adapted and configured to co-rotate both the inner sleeve and injection monitoring system about the central longitudinal axis during dose setting, and to translate the injection monitoring system along the central longitudinal axis, but not rotate said injection monitoring system around said central longitudinal axis, during injection and/or ejection of a drug from the pen injection system.

As used herein, the terms "pen injection system" and "injection pen system" are used interchangeably to designate a generally handheld pen-shaped injection system, such systems being readily well known per se and commercially available for use in the treatment of many various medical indications. These systems are also often generally designed for self-injection of a drug by the user in need of treatment for the given medical indication. This is for example the case with insulin, intended to treat the consequences of diabetes, one such example being the pen injector commercialized under the brand name FlexTouch® by Novo Nordisk. However, other drugs also fall into this category of medical devices, required for example, to address potentially life-threatening situations, and enabling immediate emergency injection of a required drug, such as anaphylactic shock treatments, anti-coagulants, opioid receptor agonists and antagonists, and the like, to the extent that it has become a common occurrence for patients suffering from, or susceptible to, such ailments to carry these devices around with them.

The injection pen system, to which the injection monitoring module according to the invention is adapted and configured for removable attachment, is equipped with a proximally located dose setting wheel and an injection activator. The dose setting wheel rotates about a central longitudinal axis of the pen injection system to allow a user to set the dose of medicament for injection. The dose setting wheel is generally rotatable in both a clockwise, and a counter-clockwise direction, these directions corresponding generally to an increase in the selected dose, and a decrease in the selected dose, to be administered, respectively. The injection activator is often represented by a push-button, usually located proximally of the dose setting wheel, and in the majority of injection pens the proximal extremity of the injection pen system. After a dose has been set, and then when a user of the injection system presses the injection activator in a distal direction, a piston is driven which is connected to a plunger in order to expel drug from a chamber within the injection pen body out through a needle that the user has inserted into an appropriate injection site, for example, the skin, fatty tissue, or muscle, depending on the type of drug to be administered. The dose setting wheel is often, but not necessarily, also coupled to the injection drive mechanism so that it also rotates as injection of the drug proceeds. The functioning of such injection systems is well known per se in the art. The monitoring module according to the present invention however, is mounted onto a pen injection system in which the dose setting wheel does not rotate during the ejection/injection phase of operation.

The injection monitoring module according to the invention, therefore, is adapted and configured to be removably attached to a proximal extremity of such an injection pen system. The expressions "removably attached", "removably attachable", "removably mounted" or "removably mountable" as might be used in the present specification are to be understood as referring to the possibility of attaching, or mounting, and subsequently removing, the injection monitoring module, for example, in the case of transferring the injection monitoring module to another pen injection system, or for example, if the monitoring module is damaged during use and requires replacement. Such attachment and subsequent removability can be achieved by providing coupling means on the monitoring module which engage in a releasable manner with the proximal extremity of the pen injection system, for example via frictional or elastic engagement, or via other releasable fastening means, such as clips, straps, screw threads and corresponding tightening rings, and the like, which engage with either the dose setting wheel, or the injection activator, or both.

The hollow main body of the injection monitoring module comprises a central longitudinal bore with a proximal extremity and a distal extremity, the bore being dimensioned to permit coaxial mounting of the hollow main body onto, and around the body of the pen injection system.

The hollow main body further comprises an inner sleeve located within the central longitudinal bore, and configured to frictionally engage with an outer surface of the dose setting wheel to co-rotate around the central longitudinal axis, without axial translation along said central longitudinal axis, but with the dose setting wheel during dose setting, such that if the inner sleeve is rotated, then so does the dose setting wheel in the same direction, and to substantially the same or identical degree of rotation. In this way, the inner sleeve can be said to co-rotate with the dose setting wheel.

The hollow main body is appropriately made of any suitable material, for example of a durable polymer or plastic material, such as high density or high impact polypropylene. Advantageously, the hollow body is made of transparent, translucent, or opaque material, in order to enable a user to apprehend and recognise any visual cues, such as light emitting diodes, that might also be provided or integrated into the injection monitoring module, where such cues can be optionally used to indicate various states of operation of the injection monitoring system. Similarly, the inner sleeve is also appropriately made of a suitable material, for example a durable polymer or high impact plastic material such as ABS.

The inner sleeve is moreover connected, or coupled, to the injection monitoring system. The connection, or coupling, between the inner sleeve and the injection monitoring system is adapted and configured to co-rotate both the inner sleeve and injection monitoring system about the central longitudinal axis during dose setting, and to translate the injection monitoring system along the central longitudinal axis, but not rotate said injection monitoring system around said central longitudinal axis, during injection and/or ejection of a drug from the pen injection system. To that end, the connection between the inner sleeve and the injection monitoring system is configured to selectively rotate about the central longitudinal axis, and then selectively translate along said longitudinal axis, the two movements being mutually exclusive of each other.

According to another object, the hollow main body further comprises a distal body portion which extends around and frictionally engages with, an outer surface of the body of the injection pen system at a location distal to the dose setting wheel. In this way, the hollow main body is maintained in position on and around the body of the pen injection system distally of the dose setting wheel, which consequently is free to rotate within the bore of the hollow body. Such a frictionally elastic configuration can, for example, be provided via an appropriate elastomeric coating or deposit located on an inner circumferential surface of the hollow main body, for example in or more zones, or alternatively as a continuous, contiguous, or semi-continuous/contiguous coating deposited on said inner circumferential surface of the hollow main body. The objective of such a frictionally elastic coating or deposit is provide frictional grip between the distal body portion and the injection pen body in order to maintain correct positioning of the hollow distal body portion against the injection pen body. Appropriate types of elastomeric materials that can provide the correspondingly frictional engagement are known in the art per se.

The injection monitoring module also comprises an injection monitoring system comprising at least one or a plurality of magnetic sensors, the injection monitoring system being located at the proximal extremity of the bore of the hollow main body. The injection monitoring system will be described in further detail below, but basically, the injection monitoring system comprises a number of different components and means that provide for monitoring of an injection state, for example, such as:

initiation of an injection operation;

termination of an injection operation, whereby termination of an injection operation is to be understood to cover both a complete administration of a selected dose of substance to be injected, or discrete injection operations in which a user only injects a part of a dose, or causes a part of the selected dose to be ejected from the pen injection system.

Furthermore, in accordance with another object of the invention, the injection monitoring system is movable along the central longitudinal axis from a first monitoring position in which the injection monitoring system is not in abutting contact with a proximal surface of the injection activator, to a second monitoring position in which the injection monitoring system is in abutting contact with a proximal surface of the injection activator. The injection monitoring system is advantageously mounted at the proximal extremity of the bore, and completely covers, or at least substantially covers, said proximal extremity of the bore.

From the above, it will be understood that the injection monitoring system can be moved from an initial position where there is no physical contact between the monitoring system and the activator button, to a different position where physical contact is established between the monitoring system and the proximal surface of the injection activator. Such movement will generally be a translational movement of the monitoring system along the central longitudinal axis from the first position to the second position. The injection monitoring module is further configured so that, after a dose has been set by rotating the inner sleeve and correspondingly coupled dose setting wheel, a translational movement along the central longitudinal axis of the injection monitoring system as described above is responsible for enabling detection or determination of an injection begin and/or end point. For example, when the monitoring system translates in a distal direction, the monitoring module can be configured to detect a begin point of injection. In an opposite manner, when the monitoring system translates in a proximal direction, thereby removing physical contact between the activator button of the pen injection system and the monitoring system, said monitoring system can be configured to detect an end point of injection or ejection of injectable substance. One way of achieving this is, for example, by determining an elapsed time during which the injection monitoring system is in physical contact with pen activator of the pen injection system. The translational movement in the reverse direction to that of injection, i.e. translation of the monitoring system in a proximal direction back towards the user's hand or thumb, can suitably be provided in such pen injection systems by making use of the recoil energy of a detent spring located inside the injection pen, after the activator button has been released by the user, for example, by removal of thumb or finger pressure on said button, either directly or indirectly, which recoil energy works against anything in contact with the proximal surface of the activator button of the pen injection system, and therefore moves the injection monitoring system away from the activator button of the pen so that the former is no longer in contact with the latter.

According to another object of the invention, the invention monitoring module comprises a magnetic field producing means, located on or within the hollow main body, at the proximal extremity of the central longitudinal bore. By the expression "located on or within the hollow main body", it is to be understood that the magnetic field producing means can be seated on a proximal facing surface of the hollow main body at the proximal extremity of the central bore, for example. Alternatively, the magnetic field producing means can be seated within a cavity or recess provided in the hollow main body at the proximal extremity of the central bore.

Various means for producing a magnetic field are known, for example, classical magnets, electromagnets, and mixed material magnets. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;

composite materials consisting of a thermoplastic matrix and isotropic neodymium-iron-boron powder, composite materials made up of a thermoplastic matrix and strontium-based hard ferrite powder, whereby the resulting magnets can contain isotropic, i.e. non-oriented, or anisotropic, i.e. oriented ferrite particles;

composite materials made of a thermo-hardening plastic matrix and isotropic neodymium-iron-boron powder, magnetic elastomers produced with, for example, heavily charged strontium ferrite powders mixed with synthetic rubber or PVC, and subsequently either extruded into the desired shape or calendered into fine sheets;

flexible calendered composites, generally having the appearance of a brown sheet, and more or less flexible depending on its thickness and its composition. These composites are never elastic like rubber, and tend to have a Shore Hardness in the range of about 40 to about 70 Shore D ANSI. Such composites are generally formed from a synthetic elastomer charged with strontium ferrite grains. The resulting magnets can be anisotropic or isotropic, the sheet varieties generally having a magnetic particle alignment due to calendering;

laminated composites, generally comprising a flexible composite as above, co-laminated with a soft iron-pole plate;

neodymium-iron-boron magnets;

steels made of aluminium-nickel-cobalt alloy and magnetized;

alloys of samarium and cobalt.

Of the above list of magnetic field producing means suitable for use in the present invention, those selected from the group consisting of neodymium-iron-boron permanent magnets, magnetic elastomers, composite materials made up of a thermoplastic matrix and strontium-based hard ferrite powder, and composite materials made of a thermo-hardening plastic matrix and isotropic neodymium-iron-boron powder, are preferred. Such magnets are known for their ability to be dimensioned at relatively small sizes whilst maintaining relatively high magnetic field strength.

Whilst the magnetic field producing means can be of any suitable general shape, for example disk-shaped, including circular, ellipsoid, or any other suitable polygonal shape, it preferably has only a single dipole, with a single pair of diametrically opposing north and south magnetic poles. Although the magnetic field producing means can also optionally be substantially disk-shaped, such a disk-shape can also preferably include magnets which have an orifice substantially in the centre of the disk to form a ring or annular shaped magnet. Such a ring or annular shaped magnet can usefully be seated on a peripheral annular and proximal facing surface of the hollow main body at the proximal extremity thereof.

According to yet another object, the hollow main body further comprises translational abutment means adapted and configured to prevent axial translational movement of the inner sleeve along the central longitudinal axis, when the injection monitoring module is in the mounted position on the injection pen system. The translational abutment means are shaped and dimensioned to prevent axial translational movement of the inner sleeve, beyond a predetermined point inside the hollow main body, along the central longitudinal axis in at least a distal direction, but also advantageously and preferably in a proximal direction along said central longitudinal axis.

According to yet another object, the translational abutment means of the hollow main body are formed as an annular groove or annular slot provided on an inside surface of the hollow main body.

According to a still further object, the translational abutment means are formed from a distally oriented surface provided on the hollow main body, and a respectively proximally oriented surface of the distal body portion, whereby the distally oriented surface and said proximally oriented surface together form a cooperating translational abutment surface for said inner sleeve.

According to another object, the inner sleeve further comprises surface engagement means located adjacent to, or substantially at, a distal extremity of said inner sleeve, wherein said surface engagement means are configured to engage with at least an inner surface of a distal body portion of the hollow main body and thereby prevent translational movement of the inner sleeve in a distal and/or proximal direction, when the injection monitoring module is in the mounted position on the injection pen system.

According to yet a still further object, the surface engagement means comprise at least one continuous projection, or a plurality of separate projections, extending radially outwardly from an outer surface of said inner sleeve.

Advantageously, and according to yet another object, the surface engagement means comprise at least one distally oriented surface, and said distally oriented surface of the surface engagement means engages with a respectively proximally oriented surface of a translational abutment means provided on an inside surface of the hollow main body.

According to yet a further object, the surface engagement means comprise at least one continuous projection, or a plurality of separate projections, extending radially outwardly from an outer surface of said inner sleeve. and the translational abutment means of the hollow main body are formed as an annular groove or annular slot provided on an inside surface of the hollow main body, wherein said annular groove or annular slot is adapted and dimensioned to receive in cooperating proximal and distal surface engagement said at least one continuous projection, or a plurality of separate projections, extending radially outwardly from an outer surface of said inner sleeve.

To summarize the above, the translational abutment means of the hollow body, and the surface engagement means of the inner sleeve, are provided with appropriately shaped surfaces and areas that cooperate with each other to prevent any translational movement in either the proximal or the distal direction, when the hollow main body is mounted on the body of the pen injection system.

According to yet another object, the inner sleeve further comprises at least one, or a plurality, of elastically deformable surfaces extending inwardly towards the central longitudinal axis from said inner sleeve, forming at least one, or a plurality, of frictionally engaging surfaces to frictionally engage with an outer surface of the dose setting wheel.

According to still another object, the at least one, or plurality, of elastically deformable surfaces extending inwardly towards the central longitudinal axis from said inner sleeve is a ring of elastically deformable material comprising a plurality of coaxially aligned, radially spaced apart teeth, extending in a same direction from said ring, and said ring is seated at a proximal extremity of the inner sleeve, with the teeth oriented to extend in a distal direction, along an outer and/or inner surface of said sleeve. Advantageously, the elastically deformable material is a suitable elastomer, such as a SEBS elastomer.

According to yet another object, the inner sleeve further comprises a plurality of coaxially aligned, radially spaced apart, openings traversing the inner sleeve from an outer surface to an inner surface thereof.

Advantageously, and according to another object, the at least one, or plurality, of elastically deformable surfaces extends through the radially spaced apart openings traversing the inner sleeve.

As will be readily understood from the preceding paragraph, the elastically deformable surfaces advantageously extend from one side, for example, an outer surface, of the inner sleeve, through the body material of the inner sleeve, and through to the other side, for example, an inner surface of the inner sleeve.

According to yet another object, the inner sleeve further comprises at least one injection monitoring system connection surface extending from an inner surface of the sleeve and projecting inwardly towards the central longitudinal axis of the bore.

Advantageously, and according to a yet further object, the at least one injection monitoring system connection surface extending from an inner surface of the sleeve and projecting inwardly towards the central longitudinal axis of the bore comprises at least one, or a plurality of, recesses provided in said inwardly projecting connecting surface.

According to yet another object, the injection monitoring system comprises a housing, and said injection monitoring system housing comprises at least one connection surface extending from said housing in a distal direction.

According to a yet still further object, the at least one injection monitoring system connection surface and the at least one injection system housing connection surface are adapted and configured to engage mutually with each other in a first position in which rotation of the injection monitoring system housing causes co-rotation of the inner sleeve, and to engage with each other in a second position in which the injection monitoring system only translates along the central longitudinal axis in a distal or proximal direction, without rotation of the injection monitoring system housing around said central longitudinal axis.

As will be readily understood from the above, the at least one injection monitoring system connection surface and the at least one injection system housing connection surface engage respectively one with the other. In the first position, the respective surfaces engage with each other to rotate together about the central longitudinal axis, for example, when a dose is being set, and in the second position, the at least one injection system housing connection surface translates against the at least one injection monitoring system connection surface in a distal, or proximal direction, depending on whether the activation button is being pressed or respectively released.

According to a further object, the at least one connection surface extending from said injection monitoring system housing comprises at least one, or a plurality of, distally extending projections, extending from a distal extremity of the housing and aligned coaxially with the central longitudinal axis.

According to yet another object, in the first position, the at least one, or plurality of, distally extending projections of the injection monitoring housing each comprise an outwardly facing connection surface which frictionally engages with a corresponding inwardly facing surface of the at least one, or plurality, of recesses provided in said inwardly projecting connecting surface.

According to a still further object, in the second position, the at least one, or plurality of, distally extending projections extending from said injection monitoring system housing further comprise at least one distally oriented contact surface which is in contact with the injection activator.

In a still further object, the injection monitoring system is further configured to determine a time elapsed during which the injection monitoring system is in physical contact with pen activator, for example, the pen activator push button, of the pen injection system.

The magnetic field production means is provided so that the magnetic field sensor will detect any changes in magnetic field, for example, due to rotational movement of the inner sleeve relative to the magnetic field producing means, during dose setting, thereby enabling the dialed dose set via the dose setting wheel to be determined. Furthermore, during injection, when digital pressure in a distal direction along the central longitudinal axis is being exerted on the housing of the injection monitoring system, the magnetic field sensor will detect changes in magnetic field due to the sensor translating along the longitudinal axis in a distal direction towards the magnetic field production means, and then in a reverse, proximal direction, as digital pressure is released from the injection monitoring system.

The magnetic field sensor is thus used to measure the magnetic field produced by the magnetic field producing means. Movement of the magnetic field sensor around the central longitudinal axis relative to the fixed hollow body proximal extremity positioning of the magnetic field production means, as the dose wheel is rotated, via the inner sleeve in contact therewith, is used to calculate or determine a dose of injectable substance in the injection pen system that has been dialed or set by the user. Once the dose has been set, activation of the proximal activator button leading to translational movement of the injection monitoring system housing, and correspondingly housed magnetic field sensors provided therewith, along the central longitudinal axis, is used to determine or calculate whether an injection has begun. Conversely, and respectively, when finger or thumb pressure on the proximal activator button is released, the recoil energy inherent in the injection pen causes the pen injection activator button to recoil, inducing translational movement of the injection monitoring system housing along the central longitudinal axis in a proximal direction, towards the thumb or fingers of the user, thereby also moving the magnetic field sensors housed within the injection monitoring system in the proximal direction. The change in magnetic field signals that the magnetic field sensors detect, when moving in this way, is processed by the injection monitoring system to determine a corresponding end of injection or ejection operation. The processing of the signals generated for begin and end of injection enables a determination of the dose actually injected between the injection begin signal and injection end signal to be made.

Means for measuring magnetic fields to determine are known generally in the art. For example, magneto-resistors are a well known means. Such magneto-resistors are often designated by their abbreviations, e.g. AMR, GMR, TMR sensors, which designate the physical mechanisms by which these sensor components function. Giant magnetoresistance (GMR) is a quantum mechanical magnetoresistance effect observed in thin-film structures composed of alternating ferromagnetic and non-magnetic conductive layers. Aniso-tropic magnetoresistance, or AMR, is said to exist in mate-rials in which a dependence of electrical resistance on the angle between the direction of electric current and direction of magnetization is observed. Tunnel magnetoresistance (TMR) is a magnetoresistive effect that occurs in a magnetic tunnel junction (MTJ), which is a component consisting of two ferromagnets separated by a thin insulator. Resistors that use these various properties are known per se.

In light of the above, the injection monitoring module and/or system according to the invention preferably uses one, or more, or a plurality of magnetometers as the one, more or plurality of magnetic field sensors. Such magne-tometers differ from the GMR, AMR or TMR sensors in that it directly measures magnetic field strength. Magnetometers measure magnetic fields in two main ways: vector magne-tometers measure the vector components of a magnetic field, and total field magnetometers or scalar magnetometers mea-sure the magnitude of the vector magnetic field.

Another type of magnetometer is the absolute magnetom-eter, which measures the absolute magnitude or vector magnetic field, using an internal calibration or known physi-cal constants of the magnetic sensor. Relative magnetom-eters measure magnitude or vector magnetic field relative to a fixed but uncalibrated baseline, and are also called vari-ometers, used to measure variations in magnetic field.

A preferred type of magnetometer therefore for use in the injection monitoring module according to the present inven-tion is an ultra low-power high performance three axis Hall-effect magnetometer. Whilst it is possible for the mag-netometer to be configured to measure magnetic field over three mutually perpendicular or orthogonal axes, it is pre-ferred in the present case that the magnetic field sensors be configured to measure magnetic fields over just two of the three orthogonal axes, for example the X and Z axes.

According to yet another object of the invention, the injection monitoring system comprises an electronic com-ponent board.

Advantageously, and according to a further object of the invention, the one or more or plurality of magnetic field sensors are electrically connected to the electronic compo-nent board. The one or more magnetic field sensors can helpfully be located on the electronic component board in diametrally opposed positions or otherwise radially distrib-uted on the electronic component board, around the central longitudinal axis, and preferably, a single magnetic field sensor is located on the central longitudinal axis.

Even more advantageously, the electronic component board comprises an integrated control and data processing unit, such as at least one micro-controller, connected elec-trically to the one or more, or plurality, of magnetic field sensors, for processing information received from the mag-netic field sensors. The electronic component board can therefore suitably be, for example, a printed circuit board of correspondingly appropriate dimensions. In the configura-tions envisaged in the present invention, such a printed circuit board is advantageously disk-shaped, with its centre corresponding to the point of intersection with the central longitudinal axis.

The electronic component board is advantageously housed within a housing that is located proximally of the hollow main body, and preferably within an injection moni-toring system housing that is located beyond the proximal extremity of the central bore. Additionally, and advanta-geously, the electronic component board is held such that a horizontal plane of the component board is located in a plane substantially orthogonal to said central longitudinal axis. The electronic component board is further located in a fixed rotational relationship in a first position, for example during dose setting, with the inner sleeve, so that rotation of the hollow main body causes the electronic component board to rotate in synchronised movement, matching that of the inner sleeve. This means that when the inner sleeve is rotated, the at least one or more or plurality of magnetometers located on the electronic component board also rotate around the cen-tral longitudinal axis. The fixed rotational relationship of the injection monitoring system to the inner sleeve in the first position can be ensured via any suitable coupling established between the inner sleeve and the injection monitoring sys-tem in said first position, as for example, has been described hereabove in regard to the coupling formed by the at least one injection monitoring system connection surface and the at least one injection system housing connection surface.

The integrated control and data processing unit, compris-ing at least one micro-controller, handles all electrical com-munication and signalling between the different electronic components of the electronic component board and the magnetic field sensors. It is also responsible for execution of the calculations enabling the precise positional location of the magnetic field sensor to be calculated and determined, as well as handling signals from an autonomous power supply and communication means integrated into the injection monitoring system, and which communicate with a local or remote data processing system, e.g. on a smartphone. Such integrated control and data processing units are known per se, and often integrate a central processing unit, a real time clock, one or more memory storage systems, and optionally communications systems or subsystems, along with other desired components.

According to yet another object of the invention, the electronic component board comprises a communications unit in electrical connection with the at least one microcontroller. Such a communications unit can be one or more of any number of communications units known per se, such as a wireless communications unit, for example, Bluetooth®, Bluetooth LE® or any other short or long range wireless communication technologies.

According to still further object of the invention, the electronic component board comprises an autonomous, and optionally rechargeable, power supply, for example a lithium ion battery, which can be easily exchanged when depleted, or alternatively, a rechargeable battery, such as a rechargeable lithium ion battery. In the event that a rechargeable battery is provided, said rechargeable battery can be charged up when depleted via a corresponding charging port, such as a USB charging port, provided in the injection monitoring module and connected to the rechargeable battery. Both non-rechargeable, i.e. single-use batteries and rechargeable batteries are generally known per se to the skilled person. Advances in charging technology have today also made wireless charging a reality, and such a wirelessly chargeable battery, for example, using an induction charging system, is also foreseen as a possibility within the objects of the invention.

These and other objects of the invention will become apparent and described in more detail in the following description relating to the figures and an example monitoring module.

BRIEF DESCRIPTION OF THE FIGURES

The invention will now be described in more detail with regard to the accompanying figures, provided for the purpose of illustration and exemplification, in which.

DETAILED DESCRIPTION OF AN EXAMPLE

Figure 1:
FIG. 1 is a schematic perspective representation of an injection monitoring module mounted on a handheld pen injection system.
Figure 2:
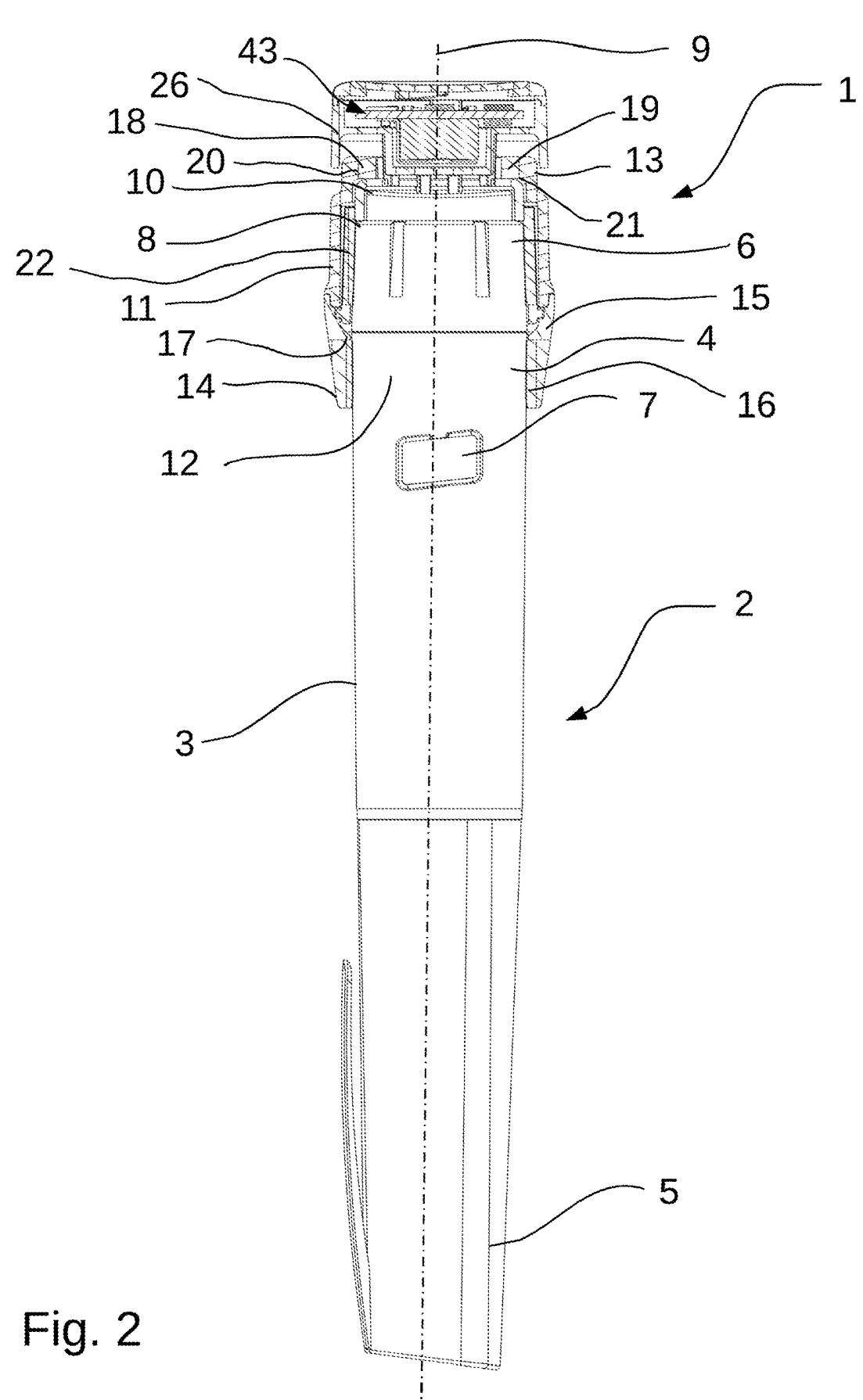
FIG. 2 is a schematic cross-sectional representation of the injection monitoring module of FIG. 1 mounted on a handheld pen injection system.

Turning now to FIGS. 1 and 2, a schematic perspective representation of an injection monitoring module (1) according to the invention is shown. The injection monitoring module (1) is mounted on a handheld injection pen system (2), which comprises a pen injection system body (3) having an outer peripheral surface (4), a pen cap (5) covering the distal extremity of the pen injection system, a dose setting or dialling wheel (6), located at the proximal extremity of the pen injection system body (3), and a dialed dose visualisation window (7), located distally of the dose setting wheel (6), and displaying the dose which has been dialed by a user of the pen injection system. The injection monitoring module (1) according to the invention is located and adjacent to the proximal extremity (8) of the injection pen system (2), in particular at least partly around and in contact with the peripheral outer surface (4), surrounding and in contact with the pen body (3) and extending in a proximal direction beyond the proximal extremity (8) of the pen body (3) and in particular beyond the dose setting wheel (6). A central longitudinal axis (9) is also illustrated, which traverses the longitudinal axial centre of both the injection monitoring module (1) and the injection pen system body (3). The injection pen system is provided with an activator button (10) proximally located from the dose setting or dialling wheel (6), as can be found in several commercially available injection pen systems. In the type of pen injection system displayed in FIGS. 1 and 2, the dose setting wheel is rotated about the central longitudinal axis (9) during dose setting, but is fixed against rotation during injection. An example of such a pen is available under the FlexTouch® insulin injection pen range supplied commercially by Novo Nordisk.

The injection monitoring module (1) comprises a hollow main body (11) which is dimensioned and sized to be coaxially mounted around the body (3) of the pen injection system (2). To this end, the hollow main body (11) comprises a central longitudinal bore (12) having a proximal extremity (13) and a distal extremity (14), and a central longitudinal axis that coincides with the central longitudinal axis (9). The hollow main body further comprises a distal body portion (15) which extends around and frictionally engages with, the outer surface (4) of the body (3) of the injection pen system (2) at a location on the pen body (3) distal to the dose setting wheel (6). Frictional engagement of the hollow main body (11) with the outer surface (4) of the pen body (3) can be achieved by providing an elastomeric frictional material (16) on an inner peripheral surface (17) of the hollow main body, such frictionally engaging materials being readily known in the art per se, to provide a push-fit or sliding-fit engagement of the distal portion (15) with the outer surface (4) of the pen body (3). The hollow main body extends in a proximal direction, above and beyond the limit of the activator button (10) of the pen injection system (2), such that the bore (12) houses both the dose setting wheel (6) and the activator button (10), and the dose setting wheel is free to rotate in the bore (12). The proximal extremity (13) of the bore corresponds so the proximal extremity of the hollow main body (11).

The hollow main body (11) further comprises a magnetic field production means (18, 19) located on or within the hollow main body (11), at the proximal extremity (13) of the central longitudinal bore (12). The magnetic field production means (18, 19) are suitably provided by a pair of single dipole magnets (18, 19), located diametrically opposite one to the other, each magnet respectively having a north (N) pole (18a, 19a) and a south (S) pole (18b, 19b), with each pair of poles being preferably oriented in axial alignment from N-S along the central longitudinal axis, with the north pole being located proximally, and the south pole distally, see for example FIG. 5. The dipole magnets (18,a, 18b, 19a, 19b) can be suitably formed into the shape of a rod, or alternatively as a disk or ring, or any other suitable shape. The magnets are located in suitably dimensioned recesses (20, 21) provided in the hollow main body (11), the recesses (20, 21) being located at the proximal extremity (13) of the body (11). Alternatively, the magnetic field production means can be a single dipole ring shaped magnet, which is seated on a peripheral proximal surface or within a corresponding annular recess of the hollow main body (11) at the proximal extremity (13) of said hollow main body. It will be understood from the above that the magnetic field production means do not rotate freely about the central longitudinal axis because the hollow main body (11) is mounted on the pen body (3) around said central longitudinal axis (9) in a fixed positional relationship with the hollow main body (11), which is frictionally held in position at the distal portion onto the outer surface (4) of the pen body (3) via the frictional engagement means (16).

The hollow main body (11) further comprises an inner sleeve (22) located within the central longitudinal bore (12), and configured to frictionally engage with an outer surface of the dose setting wheel (6) to co-rotate around the central longitudinal axis (9), without axial translation along said central longitudinal axis, but with the dose setting wheel (6) during during dose setting. The inner sleeve (22) will be described in more detail below, with regard in particular to FIGS. 5, 6A and 6B.

Figure 3:
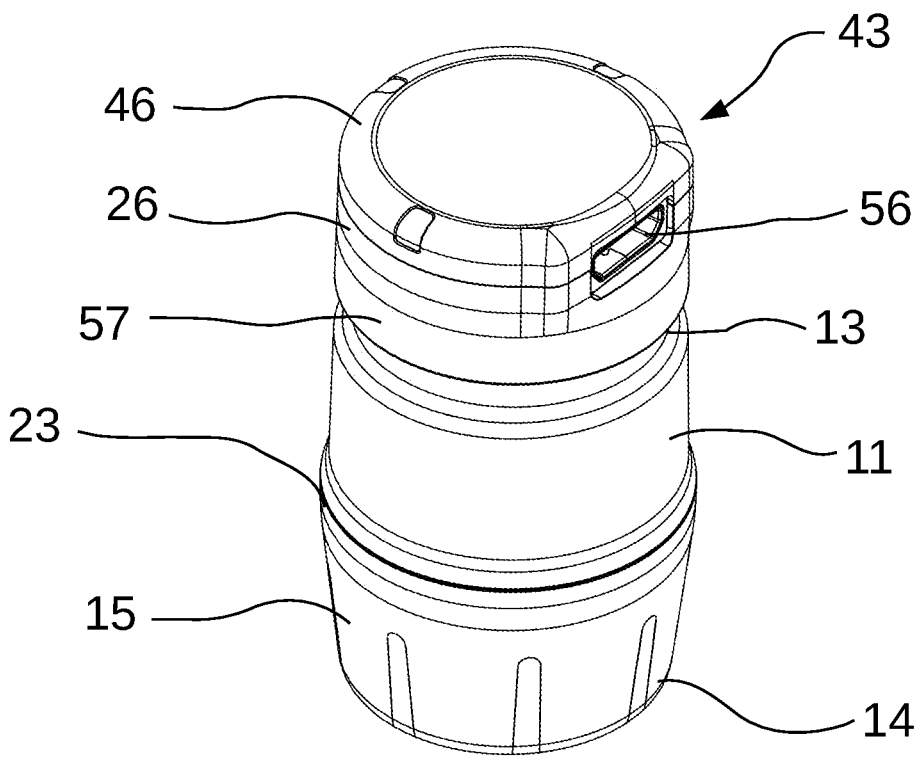
FIG. 3 is a schematic perspective representation of the injection monitoring module of FIG. 1 or FIG. 2.

The injection monitoring module is illustrated in a schematic perspective representation in FIG. 3. In this view, the hollow main body (11), distal portion (15) and respective proximal (13) and distal (14) extremities are indicated. FIG. 3 also shows that the main hollow body (11) is shaped with a gradually widening diameter from the proximal extremity towards a point (23) adjacent, or in proximity, to the distal extremity (14) of the distal portion (15). This widening diameter corresponds to a widening of the bore (12) enabling the hollow main body to be inserted onto and around the proximal extremity of the pen and fit over the dose setting wheel (6) of the pen, whilst leaving sufficient room within the bore to receive the inner sleeve (22) so that the latter may engage with an outer surface of the dose setting wheel. The distal portion (15) comprises a correspondingly shaped narrowing diameter extending from the point (23) at which the hollow main body (11) is at its widest diameter, towards the distal extremity (14). The point (23) of widest diameter is also the point at which the hollow main body (11) and distal portion (15) are suitably configured to prevent translational movement of the inner sleeve (22) along the central longitudinal axis, as will be described in more detail hereinafter with reference to FIGS. 5 6A and 6B.

Figure 4:
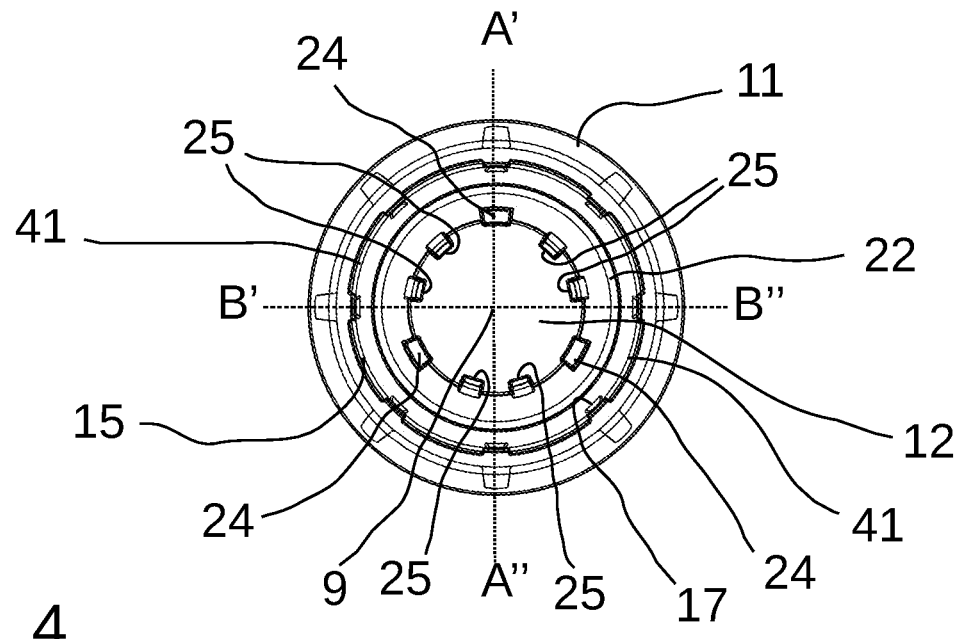
FIG. 4 is a schematic, axial representations of the injection monitoring module of FIG. 1 or FIG. 2, seen from a distal extremity thereof, along a central longitudinal axis of the module.

FIG. 4 is a schematic representation of the injection monitoring module according to the invention, when viewed from the distal extremity (14) of the distal portion (15) of the hollow main body (11) along the bore (12) and central longitudinal axis (9), the latter being represented by the intersection of cross-hairs A'-A" and B'-B". In this view, the inner peripheral surface (17) of the distal portion (15) of the hollow main body is indicated, as is the inner sleeve (22). Further represented are contact, or engagement, surfaces (24) provided respectively at a proximal extremity of the inner sleeve (22), and corresponding contact, or engagement surfaces (25) provided on an injection monitoring system housing (26) and extending in a distal direction therefrom into the bore (12), the engagement surfaces (24) and corresponding engagement surfaces (25) cooperating with each other as described in more detail hereafter.

Figure 5:
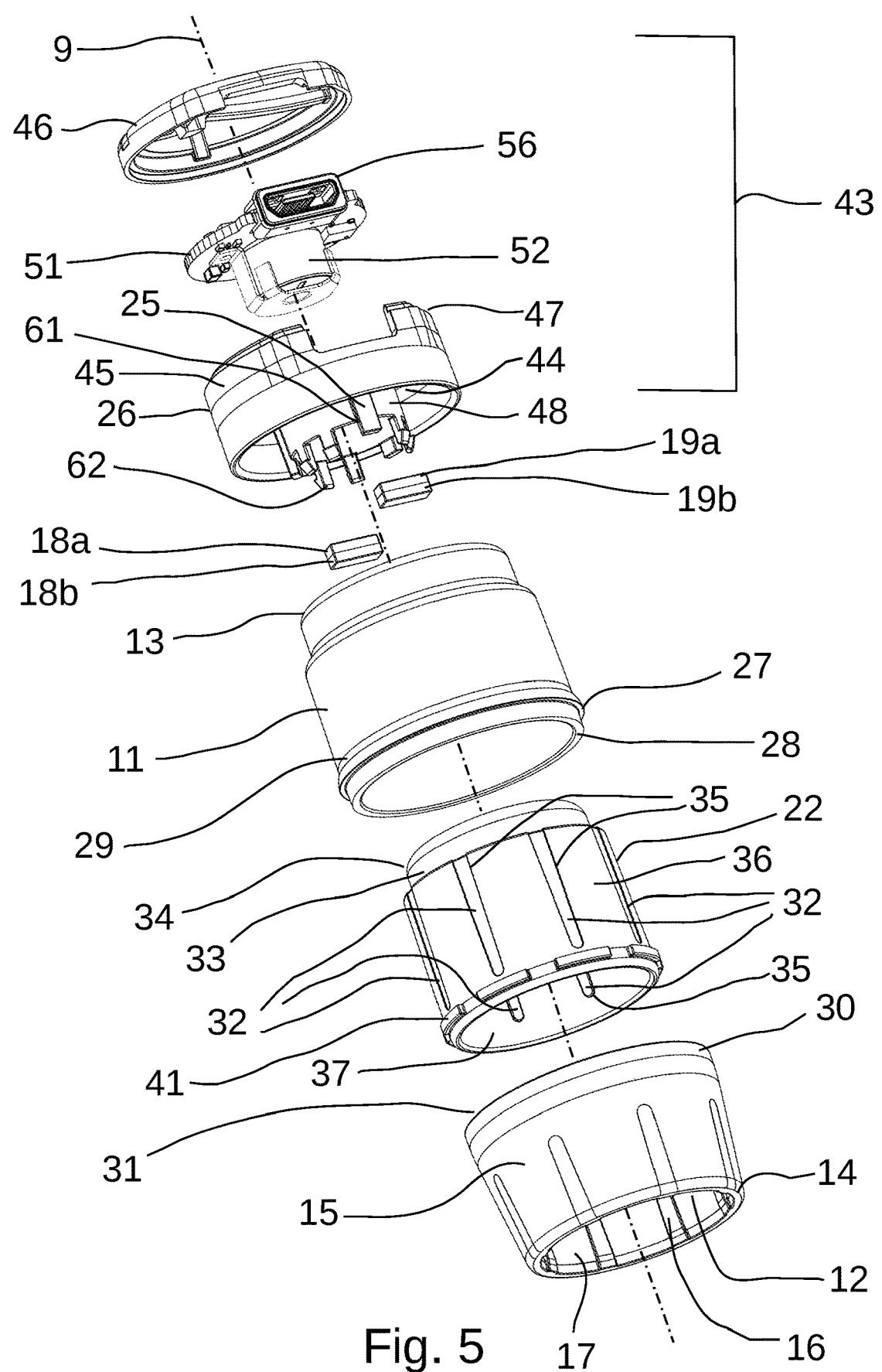
FIG. 5 is a schematic, perspective exploded view of the injection monitoring module of FIG. 1 or FIG. 2.

FIG. 5 presents a schematic exploded perspective view of the components of an exemplary injection monitoring module according to the invention. The hollow main body (11) and distal portion (15) are shown in this representation as separate components which can be assembled together when the distal portion (15) and hollow main body are mounted on the body (3) of pen injection system (2). Whilst not obligatory, such a dual component presentation is particularly advantageous in that it further facilitates insertion of the inner sleeve (22) into the bore (12), and its location against the outer surface of the body (3) of the pen injection system (2), as well as facilitating its relative positioning with regard to the distal portion (15) and hollow main body, blocking the inner sleeve from translating in a proximal or distal direction once the monitoring module is mounted on the body (3) pen injection system. To that end, the point (23) of widest diameter of both the hollow body (11) and the distal portion (15) is suitably the point at which these components are mated together on mounting of the injection monitoring module, for example, by providing a distal annular skirt (27) and proximally projecting distal annular wall (28) having a reduced diameter compared to the skirt (27), on the hollow main body (11) at a distal extremity (29) thereof, and a corresponding distally projecting annular wall (30) at a proximal extremity (31) of the distal portion, which engages with the distally projecting annular wall (28) and corresponding distal annular skirt (27). The hollow main body (11) and distal portion (15) can be suitably clipped, adhered, and/or bonded to each other at the widest point (23), for example using ultrasound welding, or any other appropriate form of bonding technique, or other engagement means enabling the hollow main body (11) and distal portion (15) to be maintained rigidly together. Alternatively, both hollow main body (11) and distal portion (15) can be provided as a single unit, appropriately dimensioned and configured to fit around and engage with, a corresponding injection pen body (3).

The inner sleeve (22) further comprises at least one, or a plurality, of elastically deformable surfaces (32) extending inwardly towards the central longitudinal axis (9) from said inner sleeve (22), forming at least one, or a plurality, of frictionally engaging surfaces (32) to frictionally engage with an outer surface of the dose setting wheel. The at least one, or plurality, of elastically deformable surfaces (32) extending inwardly towards the central longitudinal axis from the inner sleeve (22) can appropriately be provided as a ring (33) of elastically deformable material comprising a plurality of coaxially aligned, radially spaced apart teeth, extending in a same direction from said ring (33), and said ring is usefully seated at a proximal extremity (34) of the inner sleeve (22), with the teeth oriented to extend in a distal direction, along an outer and/or inner surface of said sleeve (22). Advantageously, the elastically deformable material is a suitable elastomer, such as a SEBS elastomer, generally known per se in the art. The elastically deformable surfaces (32) or teeth extend through a plurality of corresponding coaxially aligned, radially spaced apart, openings (35) traversing the inner sleeve (22) from an outer surface (36) to an inner surface (37) thereof. As will be readily understood from the above, the elastically deformable surfaces advantageously extend from one side, for example, form the outer surface (36), of the inner sleeve (22), through the body material of the inner sleeve (22), and through to the other side, for example, the inner surface (37) of the inner sleeve, thereby providing one or more frictionally engaging contact surfaces which come into contact with an outer surface of the dose setting wheel (6) of the pen injection system, ensuring that any rotation of the inner sleeve is transmitted to the dose setting wheel, and vice-versa.

Figure 6A:
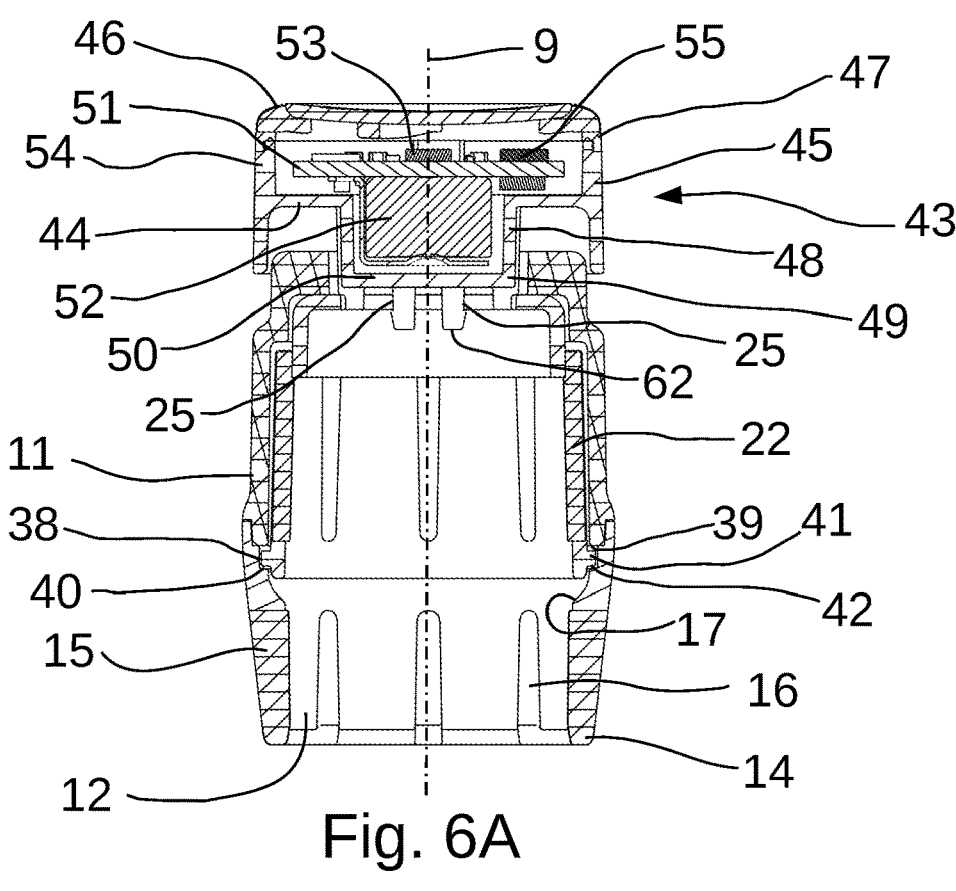
FIGS. 6A and 6B are schematic, cross-sectional representations of the injection monitoring module of FIG. 1 or FIG. 2 in a first and second position about the central longitudinal axis in a dose setting position.
Figure 6B:
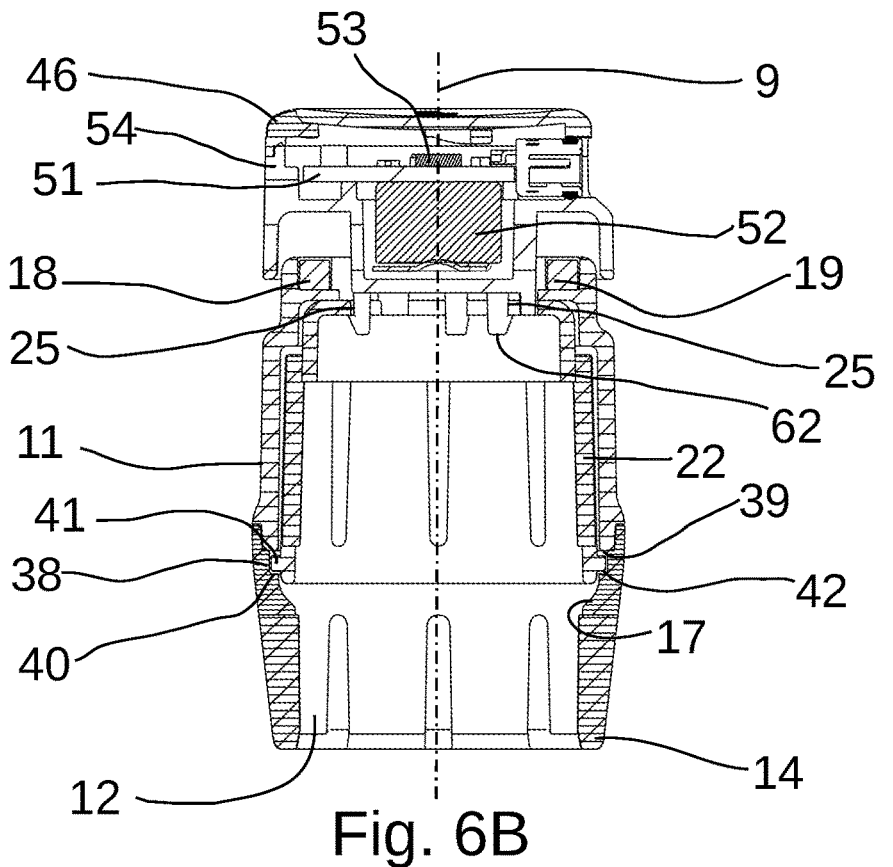

As has been mentioned above, and as illustrated in greater detail in FIGS. 6A and 6B, which are representative cross-sectional views of the injection monitoring device according to the invention, the inner sleeve (22) is blocked against translational movement in a proximal or distal direction along the central longitudinal axis (9). FIGS. 6A and 6B represent the injection monitoring module in the first, or dose setting position, that is, the position in which the monitoring module would be found after mounting on the pen injection body. The difference between FIG. 6A and FIG. 6B is merely one of the rotation of the cross-section about the central longitudinal axis (9). The hollow main body (11) thus further comprises translational abutment means (38) adapted and configured to prevent axial translational movement of the inner sleeve (22) along the central longitudinal axis, when the injection monitoring module (1) is in the mounted position on the injection pen system (2). The translational abutment means (38) are shaped and dimensioned to prevent axial translational movement of the inner sleeve, beyond a predetermined point (23) in, or on, the hollow main body, along the central longitudinal axis (9) in at least a distal direction, but also advantageously and preferably in a proximal direction along said central longitudinal axis (9). To that end, the translational abutment means of the hollow main body (11) are formed as an annular groove (38) or annular slot provided on an inside surface (17) of the hollow main body (11). The annular groove (38) can be suitably formed by the cooperating surfaces formed from a distally oriented surface (39) provided on the hollow main body (11), and a respectively correspondingly proximally oriented surface (40) of the distal body portion (15).

Additionally, the inner sleeve further comprises surface engagement means (41) located adjacent to, or substantially at, a distal extremity of said inner sleeve, wherein said surface engagement means are configured to engage with at least an inner surface of the distal body portion (15) and the hollow main body (11), for example, the annular groove (38) formed by distally oriented surface (39) and proximally oriented surface (40), and thereby prevent translational movement of the inner sleeve in a distal and/or proximal direction, when the injection monitoring module (1) is in the mounted position on the injection pen system (2). To that end, the surface engagement means (41) can appropriately be formed by at least one continuous projection (41), or a plurality of separate projections (41a, 41b, 41c, etc), extending radially outwardly from the outer surface (36) of said inner sleeve (22). Said projections (41) comprise at least one distally oriented surface (42), which distally oriented surface (42) engages with a respectively proximally oriented surface (40) of the annular groove (38) provided on the inside surface (17) of the hollow main body (11). The interaction between the cooperating surfaces of the projections (41) with the annular groove (38) and respective surfaces (39, 40) prevents any substantial translational movement of the inner sleeve along the central longitudinal axis when the injection monitoring module is mounted on the pen injection system, but said groove (38) and projections (41) are nonetheless appropriately and correspondingly dimensioned to permit rotation of the inner sleeve (22) about the central longitudinal axis (9), the projections (41) being free to move around said axis (9) within the groove (38) when a rotational force or effort is applied to the inner sleeve (22), for example, during dose setting.

As is visible from the figures, in particular, FIGS. 5, 6A and 6B, the inner sleeve is furthermore connected to an injection monitoring system (43), indicated in square brackets and comprising several components, among which an injection monitoring system housing (26). The injection monitoring system housing (26) is shaped and configured to resemble a cup with a stem, with a base wall (44) extending over substantially the same, or similar diameter as the hollow main body (11), and substantially perpendicular to the central longitudinal axis, and a first annular wall (45) extending from an outer periphery of the base wall (44), in a proximal direction away from said base wall (44), thereby forming a cup shaped part with an inner volume that is closed by a proximal cap (46) forming a push button, which is snap or push-fitted or adhered, or otherwise affixed onto said proximally extending first annular wall (45) at the proximal extremity (47) of said first annular wall. The base wall (44) further comprises a second annular wall (48) extending from the base wall (44) in a distal direction from a location radially spaced apart from the central longitudinal axis (9), and having a diameter smaller than the diameter of the bore (12) of the hollow main body. The second annular wall (48) is closed at its distal extremity (49) by a cross wall (50) to form the stem of the cup. The stem of the cup sits within the bore (12) of the hollow main body. The injection monitoring system housing (26), as defined by the cup shaped inner volume, receives and seats an electronic component board (51). The internal volume of the stem formed by the second annular wall (48) and the cross wall (50) receives an autonomous power supply (52), such as a single use, or rechargeable, battery, for example, a lithium ion battery electrically connected to the electronic component board (51) to provide power thereto. The electronic component board (51) is appropriately and generally a printed circuit board of suitable dimensions to be located within the internal volume of the cup formed by the base wall (44) and proximally extending first annular wall (45). The injection monitoring housing (26) optionally further comprises a light guide window (54), integrated into or being part of, the first annular wall (45), for example, a translucent, opaque, or transparent material shaped and with crystalline properties selected to guide a lightwave from the inside volume of the cup, for example, as produced by an optionally present light emitting diode or other lightwave producing component, to the outside of the injection monitoring system housing (26).

The electronic component board (51) further comprises at least one magnetometer (53), advantageously located on the central longitudinal axis, and in the case of a substantially circular shaped component board, substantially in the centre thereof so that it is aligned on the central longitudinal axis. In addition to the magnetometer (53), the injection monitoring system (43) also comprises an integrated control and data processing unit (55) electrically connected to the magnetometer (53) for processing information received from the magnetometer. The integrated control and data processing unit (55) handles all electrical communication and signalling between the different electronic components of the injection monitoring system. It is also responsible for execution of the dose management system and calculations enabling the precise positional location of the magnet to be calculated and determined, as well as handling signals from the autonomous power supply (52). The electronic component board can further be connected to a USB port (56), which can be configured as a power supply recharging port for a rechargeable battery (52), and/or be configured to enable basic setup of any programmable memory on the electronic component board, or to configure the data processing unit (55). The integrated control and data processing unit (55) usually also comprises communication means which communicate with a local or remote data processing system, e.g. on a smartphone, such as a wireless communications circuit, for example, a Bluetooth® or BluetoothLE® wireless communications system, to name but two of many types of suitable communications means. The integrated control and data processing unit (55) can suitably be programmed remotely, upon first use, or receive information and updates, in a similar way to other electronic devices today containing integrated control and data processing units, for example, wirelessly, or via any other suitable link, such as the USB port (56). Such integrated control and data processing units are known per se, and often integrate a central processing unit, a real time clock, one or more memory storage systems, and optionally communications systems or subsystems, along with other desired components. The electronic component board (51) is seated or located within the cup formed by the base wall (44) and first annular wall (45) of the injection monitoring system housing (26), substantially along the horizontal plane of the circuit board, i.e. generally orthogonal and perpendicular to the central longitudinal axis (9).

The injection monitoring housing further comprises a third annular wall (57) extending from the base wall (44) at the periphery of said base wall (44) in a distal direction towards the hollow main body (11). This third annular base wall (57) provides axial stabilisation for the injection monitoring system housing (26), in particular to the extent that it is dimensioned to surround an outer peripheral circumference of the hollow main body at the proximal extremity (13) thereof, both in the first, dose setting position, and during activation of the activator button (10), in other words, during injection and/or ejection of a substance from the injection pen system, as can be seen in FIGS. 6A, 6B and FIG. 7.

Figure 7:
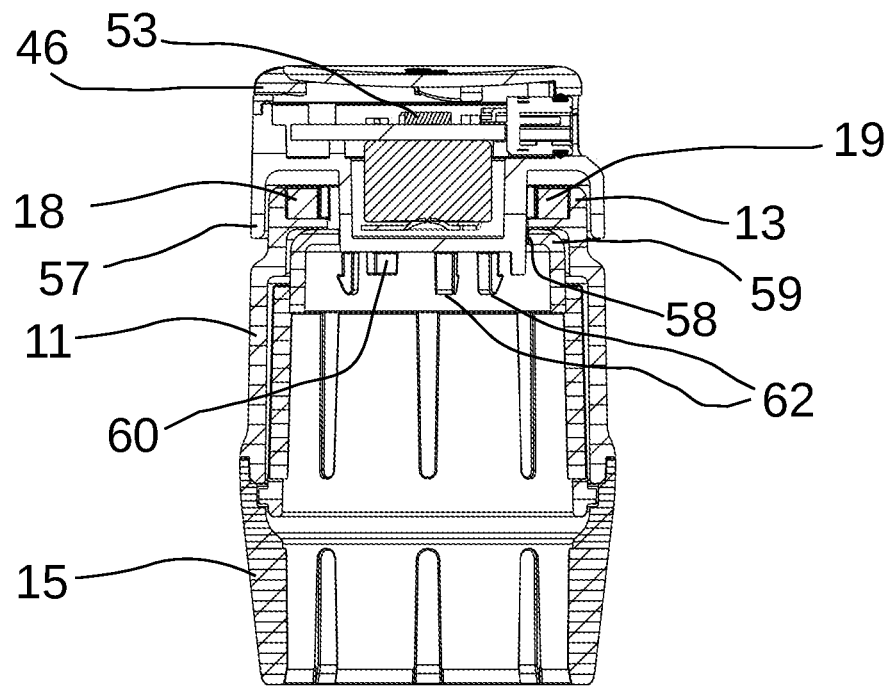
FIG. 7 is a schematic, cross-sectional representation of the injection monitoring module of FIG. 1 or FIG. 2, in a dose ejecting or administering position.
Figure 8:
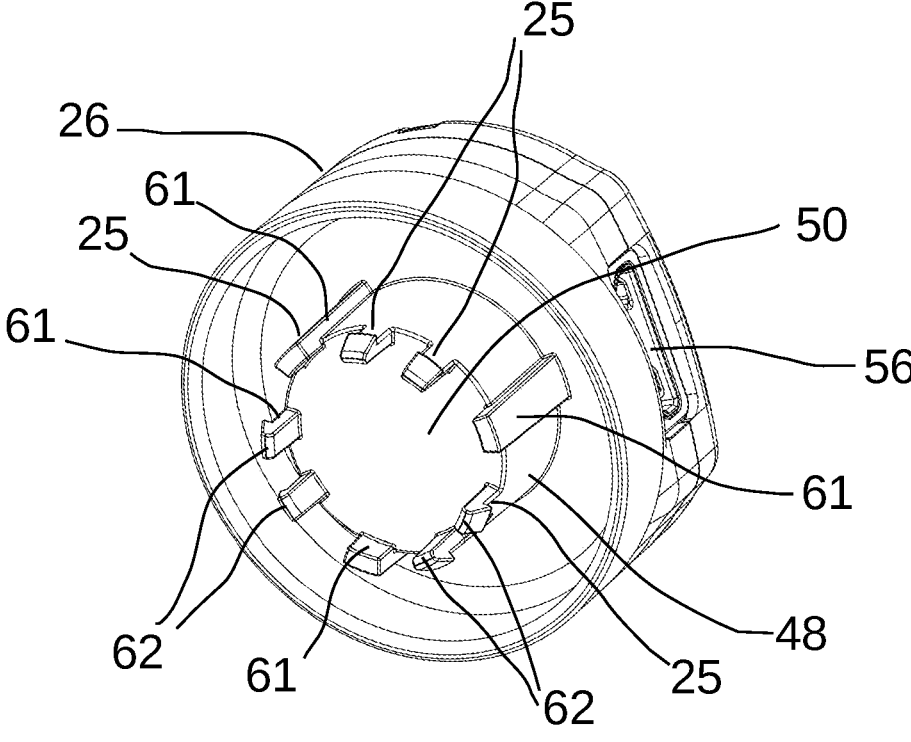
FIG. 8 is a schematic, perspective view of an injection monitoring system housing forming part of the injection monitoring module of FIG. 1 or FIG. 2, and also represented in FIG. 5.

FIG. 7, and particularly FIG. 8, both show some of the detail relating to the physical connection between the inner sleeve (22) and the injection monitoring system housing (26). In particular, this connection is adapted and configured to enable co-rotation of both the inner sleeve (22) and the injection monitoring system housing (26) about the central longitudinal axis (9) in the first position, that is, during dose setting, and then to permit translation, but not rotation, of the injection monitoring system housing (26) along the central longitudinal axis (9), in the second position, that is, during injection and/or ejection of a drug from the pen injection system.

The connection between the inner sleeve (22) and the injection monitoring system housing is advantageously provided through a series of interacting and mutually cooperating connection surfaces (24, 25). Accordingly, the inner sleeve (22) is provided with at least one injection monitoring system connection surface (24), that is to say a surface that connects, contacts, or engages with said injection monitoring system, and which connection surface extends from an inner surface of the sleeve (22) and projects inwardly towards the central longitudinal axis of the bore (12). As illustrated in FIG. 7, in which the injection monitoring module (1) has been moved into the ejection or injection position, activating the activator button of the pen injection system, the connection surface (24) is an annular surface formed on the innermost peripheral edge (58) of an annular shoulder (59) that extends from the proximal extremity of the inner sleeve (22) radially inwardly into the bore (12). Such a connection surface (24) usefully further comprises at least one, or a plurality of, recesses (60) provided in said inwardly projecting connecting surface.

In counterpart, the injection monitoring housing (26) comprises at least one corresponding connection surface (25) extending from said housing (26) in a distal direction. As illustrated in the Figures, the connection surfaces (25) extending distally from the injection monitoring housing (26) are provided as a plurality of one or more projecting nubs (61), one or more of which are further provided with distal extremity contact surfaces (62). The projecting nubs (61) extend either from the base wall (44), and/or from the distal extremity (49) of the second annular wall (48), and/or the cross wall (50), and are radially spaced apart from each other around the central longitudinal axis (9). Some of the nubs (61), for example, three nubs, are shaped and dimensioned to slot into the corresponding recesses (60) provided in the annular inwardly projecting shoulder (59). The remaining nubs (61), thereby providing a rotational lock between the inner sleeve (22) and the injection monitoring system housing (26) in the first, dose setting position. The remaining nubs (61) project even further in the distal direction, and have sufficient length to be able to engage and contact the activator button (10) of the pen injection system when an injection and/or ejection operation is carried out using the pen injection system, for example when administering a dose of injectable substance, such as a drug. This is the case when the injection monitoring module is moved from the first, dose setting position to the second, dose ejection and/or injection position.

The mutually cooperating connection or contact surfaces (24, 25) thus engage with each other in the first position, in which rotation of the injection monitoring system housing (26) by the user using fingers and/or thumb as per the usual mode of operation for an injection pen system of the type described, causes co-rotation of the inner sleeve (22), allowing a dose to be set, because the inner sleeve also engages the outer surface of the dose setting wheel (6). Once the dose has been set, pressing the cap in a distal direction with a thumb and/or finger, will cause connection surfaces (24, 25) to slidingly engage one against the other in a translational movement along the central longitudinal axis (9) without any rotational movement. In doing so, the nubs (61) are moved along the central longitudinal axis (9) within the bore (12) until the distal extremity contact surfaces (62) come into contact with the activator button (10). This corresponds to the second position. As the longitudinal distance between no contact of the distal surfaces (62) and contact of the distal surfaces (62) with the activator button is only a few millimetres, and this axial translational travel distance is a known value, the data processing unit can be configured to calculate how long the distal extremity contact surfaces remain in contact with the activator button. For example, in such a situation, one can use an elapsed time method, which is calibrated for predetermined detectable changes in magnetic field along the longitudinal axis as the magnetic field sensor is moved from the first, dose setting position, to the second, dose ejection/injection position, and then moved back again due to the recoil energy imparted to the activator button (10) of the pen injection system (2) by the internal detent spring of such pen injection systems. Calculation of the elapsed time by the data processing unit also enables further preprogrammed calculations to determine an injection start point and a corresponding injection end point, which are temporarily stored in the data processing unit of the injection monitoring module for later transmission via the communications unit, for example, via wireless communication, to a remote device, such as a smartphone, tablet or other remote computing device.

As an example of how the injection monitoring module can be used, the following description is provided:

the monitoring module is mounted on a pen injection device, e.g. a Flextouch® insulin pen;

a user rotates the injection monitoring system housing using fingers and/or thumb of one hand, holding the body of the pen in the other;

rotation of the injection monitoring system housing (26), which is rotationally locked with the inner sleeve (22) via the connecting surfaces (24, 25), causes rotation of the dose setting wheel (6) of the injection pen due to the frictional contact between the inner sleeve and the outer surface of the dose setting wheel (6);

rotation of the magnetometer (53) around the central longitudinal axis (9) during dose setting causes the magnetometer (53) to register variations in magnetic field, as a function of the angular position of the magnetometer in relation to the magnets, with the data processing unit;

when the user presses on the proximal cap (46), the injection monitoring housing (26) translates in a distal direction along the central longitudinal axis (9);

as a result of this translational movement, the magnetometer also translates along said axis, in the distal direction, and any changes in detected magnetic field are signalled to the data processing unit;

the distal contact surfaces (62) of the nubs (61) come into contact with the activator button, thereby initiating an injection/ejection operation;

no further translational movement in the proximal direction occurs during the injection/ejection operation, as the activator button has predetermined constrained limit of longitudinal axial movement, usually less than 1 millimeter, when the user releases thumb or finger pressure on the cap (46), the activator button recoils under the impetus of the recoil energy imparted to it by the pen system just enough to cause said recoil energy to be transmitted to the distal surfaces (62) of the nubs (61), thereby causing the injection monitoring housing (26) to move in a proximal direction from the second position, back to the first position;

the magnetometer moves away from the magnets the same translational distance along the central axis, and signals corresponding magnetic field changes to the data processing unit;

the data processing unit then calculates, for example using a time elapsed correlation method based on the known distance travelled and the signalled magnetic fields, to determine an injection start point, an injection end point, and the actual dose ejected and/or injected.

The invention claimed is:

1. Injection monitoring module adapted and configured to be removably mounted to a proximal extremity of an injection pen system for delivery of a drug, the injection pen system having a pen body, a proximally located dose setting wheel connected to said body, and an injection activator, the dose setting wheel being rotatable about a central longitudinal axis of the pen injection system during dose setting and fixed against rotation during injection, wherein the injection monitoring module comprises:

a hollow main body adapted and configured to be coaxially mounted around the body of the pen injection system, the hollow main body comprising a central longitudinal bore having a proximal extremity and a distal extremity, and a central longitudinal axis;

a magnetic field production means, located on or within the hollow main body, at the proximal extremity of the central longitudinal bore;

an injection monitoring system comprising at least one or a plurality of magnetic sensors, the injection monitoring system being located at the proximal extremity of the bore of the hollow main body;

the hollow main body further comprising an inner sleeve rotationally located within the central longitudinal bore, and configured to frictionally engage with an outer surface of the dose setting wheel to co-rotate around the central longitudinal axis with respect to said hollow main body, without axial translation along said central longitudinal axis, with the dose setting wheel during dose setting;

wherein the inner sleeve is rotationally locked to the injection monitoring system such that rotation of said injection monitoring system causes rotation of said inner sleeve with respect to said hollow main body; and wherein the injection monitoring system is configured for translational movement with respect to said inner sleeve along the central longitudinal axis, during injection and/or ejection of a drug from the pen injection system.

2. Injection monitoring module according to claim 1, wherein the hollow main body further comprises a distal body portion which extends around and frictionally engages with, an outer surface of the body of the injection pen system at a location distal to the dose setting wheel.

3. Injection monitoring module according to claim 2, wherein the hollow main body further comprises translational abutment means adapted and configured to prevent axial translational movement of the inner sleeve along the central longitudinal axis, when the injection monitoring module is in the mounted position on the injection pen system.

4. Injection monitoring module according to claim 3, wherein the translational abutment means of the hollow main body are formed as an annular groove or annular slot provided on an inside surface of the hollow main body.

5. Injection monitoring module according to claim 4, wherein the translational abutment means are formed from a distally oriented surface provided on the hollow main body, and a respectively proximally oriented surface of the distal body portion, said distally oriented surface and said proximally oriented surface forming together a cooperating translational abutment surface for said inner sleeve.

6. Injection monitoring module according to claim 1, wherein the inner sleeve further comprises surface engagement means located adjacent to, or substantially at, a distal extremity of said inner sleeve, wherein said surface engagement means are configured to engage with at least an inner surface of a distal body portion of the hollow main body and thereby prevent translational movement of the inner sleeve in a distal and/or proximal direction, when the injection monitoring module is in the mounted position on the injection pen system.

7. Injection monitoring module according to claim 6, wherein where the surface engagement means comprise at least one continuous projection, or a plurality of separate projections, extending radially outwardly from an outer surface of said inner sleeve.

8. Injection monitoring module according to claim 6, wherein the surface engagement means comprise at least one distally oriented surface, and said distally oriented surface of the surface engagement means engages with a respectively proximally oriented surface of a translational abutment means provided on an inside surface of the hollow main body.

9. Injection monitoring module according to claim 6, wherein the surface engagement means comprise at least one continuous projection, or a plurality of separate projections, extending radially outwardly from an outer surface of said inner sleeve and the translational abutment means of the hollow main body are formed as an annular groove or annular slot provided on an inside surface of the hollow main body, wherein said annular groove or annular slot is adapted and dimensioned to receive said at least one continuous projection, or a plurality of separate projections, extending radially outwardly from an outer surface of said inner sleeve.

10. Injection monitoring module according to claim 1, wherein the inner sleeve further comprises at least one, or a plurality, of elastically deformable surfaces extending inwardly towards the central longitudinal axis from said inner sleeve, forming at least one, or a plurality, of frictionally engaging surfaces to frictionally engage with an outer surface of the dose setting wheel.

11. Injection monitoring module according to claim 10, wherein the at least one, or plurality, of elastically deformable surfaces extending inwardly towards the central longitudinal axis from said inner sleeve is a ring of elastically deformable material comprising a plurality of coaxially aligned, radially spaced apart teeth, extending in a same direction from said ring, and said ring is seated at a proximal extremity of the inner sleeve, with the teeth oriented to extend in a distal direction, along an outer and/or inner surface of said sleeve.

12. Injection monitoring module according to claim 10, wherein the inner sleeve further comprises a plurality of coaxially aligned, radially spaced apart, openings traversing the inner sleeve from an outer surface to an inner surface.

13. Injection monitoring module according to claim 12, wherein the at least one, or plurality, of elastically deformable surfaces extends through the radially spaced apart openings traversing the inner sleeve.

14. Injection monitoring module according to claim 1, wherein the inner sleeve further comprises at least one injection monitoring system connection surface extending from an inner surface of the inner sleeve and projecting inwardly towards the central longitudinal axis of the bore.

15. Injection monitoring module according to claim 14, wherein the at least one injection monitoring system connection surface extending from the inner surface of the inner sleeve and projecting inwardly towards the central longitudinal axis of the bore comprises at least one, or a plurality of, recesses provided in said connecting surface.

16. Injection monitoring module according to claim 15, wherein the injection monitoring system comprises a housing, and said injection monitoring system housing comprises at least one connection surface extending from said housing in a distal direction.

17. Injection monitoring module according to claim 16, wherein the at least one injection monitoring system connection surface and the at least one injection system housing connection surface are adapted and configured to engage mutually with each other in a first position in which rotation of the injection monitoring system housing causes co-rotation of the inner sleeve, and to engage with each other in a second position in which the injection monitoring system only translates along the central longitudinal axis in a distal or proximal direction, without rotation of the injection monitoring system housing around said central longitudinal axis.

18. Injection monitoring module according to claim 17, wherein the at least one connection surface extending from said injection monitoring system housing comprises at least one, or a plurality of, distally extending projections, extending from a distal extremity of the housing and aligned coaxially with the central longitudinal axis.

19. Injection monitoring module according to claim 18, wherein, in the first position, the at least one, or plurality of, distally extending projections of the injection monitoring housing each comprise an outwardly facing connection surface which frictionally engages with a corresponding inwardly facing surface of the at least one, or plurality, of recesses provided in said inwardly projecting connecting surface.

20. Injection monitoring module according to claim 18, wherein, in the second position, the at least one, or plurality of, distally extending projections extending from said injection monitoring system housing further comprise at least one distally oriented contact surface which is in contact with the injection activator.

21. Injection monitoring module according to claim 1, wherein the injection monitoring system is further configured to determine a time elapsed during which the injection monitoring system is in physical contact with pen activator of the pen injection system.

22. Injection monitoring module according to claim 1, wherein the injection monitoring system comprises an electronic component board, the electronic component board comprising a rechargeable power supply, at least one microcontroller in electrical connection with the one or plurality of magnetic field sensors, and a communications unit in electrical connection with the at least one microcontroller.

* * * * *